United States Patent [19]

Kjærgaard et al.

[11] Patent Number: 5,671,615
[45] Date of Patent: Sep. 30, 1997

[54] FIXATION PANTY BRIEF

[76] Inventors: Finn Kjærgaard, Øgaardshøjen 1B, DK-8800 Viborg; Johannes Nyvang Kristensen, Læsøgade 3, DK-7430 Ikast, both of Denmark

[21] Appl. No.: 545,620
[22] PCT Filed: May 3, 1994
[86] PCT No.: PCT/DK94/00175
   § 371 Date: Nov. 2, 1995
   § 102(e) Date: Nov. 2, 1995
[87] PCT Pub. No.: WO94/24978
   PCT Pub. Date: Nov. 10, 1994

[30] Foreign Application Priority Data

May 3, 1993 [DK] Denmark ............... 0499/93

[51] Int. Cl.$^6$ ............................................. A41B 9/04
[52] U.S. Cl. ............................ 66/177; 2/401; 2/406
[58] Field of Search .......................... 2/400, 401, 406; 66/169 R, 171, 172 R, 172 E, 175, 176, 177

[56] References Cited

U.S. PATENT DOCUMENTS

| | | |
|---|---|---|
| 3,312,981 | 4/1967 | McGuire et al. . |
| 3,566,624 | 3/1971 | Burleson .................... 66/177 |
| 4,695,279 | 9/1987 | Steer ............................ 2/406 |

FOREIGN PATENT DOCUMENTS

| | | |
|---|---|---|
| 0407100 | 8/1994 | European Pat. Off. . |
| 2531403 | 7/1975 | Germany . |
| 2656403 | 12/1976 | Germany . |
| 2518508 | 12/1982 | Germany . |

Primary Examiner—C. D. Crowder
Assistant Examiner—Larry D. Worrell, Jr.
Attorney, Agent, or Firm—Frost & Jacobs

[57] ABSTRACT

A fixation panty brief (7, 29) comprises a tubular body portion (10) and a crotch portion (11). The panty brief comprises a waistband portion (16) for encircling the body of the user and at the same time a snug fit to the user known from ordinary circular knitted panty briefs. The body portion (10) and the crotch portion (11) of the fixation panty brief are produced in one singular piece by circular knitting and at the same time a looser knitting has been used in one or several areas for providing containment and fixation pockets (21, 30) for containing a diaper or hip protection bowls which are held in place in that the delimiting edge areas have an elastic and firm knitting which forms a close fit to the user's body. The edge areas will consequently be in firm contact with the user's body while the pockets (21, 30) are able to contain a diaper or a hip protection bowl. A panty brief may also comprise a loose net-like structure for providing an inspection window (5). In this manner it is possible to see a moisture indicator on a diaper (20). The panty brief is advantageous in that it provides rich user comfort and may be manufactured with a very low degree of afterfashioning.

11 Claims, 3 Drawing Sheets

FIXATION PANTY BRIEF

TECHNICAL FIELD

The present invention relates to a fixation panty brief comprising a tubular body portion and a crotch portion situated between two leg openings at one end of the tubular body portion, which comprises a waistband portion at its other end, wherein the body portion and the crotch portion are produced in one singular piece by circular knitting and wherein, in one or several areas of the brief, a more loose knitting is provided.

Fixation panty briefs are known which are produced by Raschel knitting and allow secure containment and fixation, e.g. of diapers, in the panty brief crotch portion. These Raschel-knitted panty briefs may be produced by machines, ready for Use without any other kind of afterfashioning but fixation.

Circular knitted panty briefs are known as well. The only circular knitted panty briefs know so far, however, have been for ordinary use, i.e. panty briefs which have not been suitable for fixation. In order to use circular knitted or partly circular knitted panty briefs for fixation, it has previously been suggested to use combined panty briefs.

Thus, from U.S. Pat. No. 3,312,981 a fixation panty brief is known which is produced from a tubular body portion which eliminates the need for side seams. This body portion is knitted together with a flat knitted member which makes up a crotch portion and, when secured to the body portion, forms the leg openings. This known panty brief further comprises a nonstretchable strap which extends downward from the waistband portion to the crotch portion in order to secure correct positioning of a sanitary napkin in the crotch portion.

The fixation panty brief described in the U.S. publication is disadvantageous in that it necessitates the manufacture of three separate members which are subsequently to be mutually secured in order to form the finished panty brief. This is both time-consuming and requires much exactness in the manufacture and securing of the different members. The panty brief will furthermore give the consumer a poor comfort due to the use of the nonstretchable strap and the two transverse seams between the body portion and the crotch portion. Furthermore, the disclosed panty brief is only applicable as a fixation panty brief for napkins, From EP-A-0,407,100 a fixation panty brief is also known. This panty brief is produced from a tubular body. The panty brief disclosed comprise in half of the area a loose knitting in order to provide the necessary shaping to the front and the back side of a larger sized user. The panty brief could contain a pad or diaper which due to the elasticity of the brief would be held against the user. However, the fixation is not effective. Even though only a small seam is used in the crotch area then this seam would press against the pad and tends to displace it out of position as the wearer moves. Accordingly, the panty brief would not provide a secure fixation even though is is possible to make a necessary shaping for larger sized users.

Disclosure of the Invention

It is the object of the present invention to remedy the disadvantages described above by providing a panty brief of the type mentioned in the introduction which may be produced by circular knitting as separate units with a minimum of afterfashioning and which panty brief simultaneously gives a secure fixation of an item.

Background Art

This is achieved according to the present invention by a panty brief of the type mentioned in the introduction which is characterized in that the area(s) having a more loose knitting is (are) used for forming containment and fixation pockets the delimiting edge areas of which have an elastic and firm knitting for providing a snug fit to the user's body.

With such a panty brief it is made possible in a surprisingly simple manner to manufacture a panty brief with very high user comfort since only a single very short seam is required extending across the crotch portion between the leg openings as also disclosed in EP-A-0,407,100. Thus, it is possible to produce the panty briefs in circular knitting machines. Following any cutting between the leg openings, all that is required to form the finished panty briefs is said seam in the crotch portion and possibly securing an elastic border along the leg openings. Cutting and stitching are provided in one operation.

As the fixation panty brief is manufactured in one piece, there are no requirements of adapting various parts, and neither will there be any disadvantages due to missing or incorrect stitching of the two parts.

The looser knitting for providing containment and fixation pockets may optionally be positioned in the crotch portion in order to form a diaper fixation panty brief or adjacent the hip sockets of a user when the panty brief is in use in order to form a hip fixation panty brief.

Thus, with the panty brief according to the invention it is possible to produce a panty brief which is able to hold different products by using the looser knitting with the delimiting firm knitting in different areas.

As a traditional diaper fixation panty brief the containment and fixation pocket will extend throughout the crotch portion both at the front and the back of the User and form a banana-shaped pocket. Due to the firm knitting in the edge area of the pocket, close contact is achieved and consequently liquid is prevented from leaking from the edges of the diaper. It is also possible to manufacture the panty brief as a fixation panty brief for a diaper to be used by urinary incontinent male persons. This is achieved by positioning the containment and fixation pocket at the front of the panty brief in the upper part of the crotch portion and extending upward on the front of the panty brief.

When the panty brief is used as a diaper fixation panty brief, it may advantageously comprise a loose net-like structure in a small area at the front of the user and possibly also at the back of the user. Through this transparent knitting it is made possible to make an inspection of a moisture indicator on a diaper. Thus, when in use it will be possible to examine from the outside whether a diaper needs to be changed or not. This will be a convenience for the staff of nurseries, hospitals, rest homes, and in private homes where it is possible to find out visually, and without having to remove the diaper fixation panty briefs, whether a change of diaper is necessary.

The fixation panty briefs according to the invention will feel very comfortable to the user. This is partly because the panty brief is produced without side seam and partly because the panty brief will be manufactured with the excellent fit known from ordinary circular knitted panty briefs.

BRIEF DESCRIPTION OF THE DRAWINGS

The invention will now be described in further detail with reference to the attached drawing, in which.

DETAILED DESCRIPTION OF THE INVENTION

First it should be noted that the knitting machine used for knitting a fixation panty brief according to the invention is a known circular knitting machine, e.g. of the type Santoni SM4 marketed by the Italian company Santoni.

The circular knitting machine is equipped with a set of latch needles and sinkers for overhang for making a double ribbed edge in the waistband portion of the panty brief Such as explained below. Step motors are mounted in this machine so that it is possible to control the stitch length. As the machine is well known, a description of the use and the settings of the machine will not be explained in detail. When knitting, it is possible to control whether the needles should go up or not so as to obtain different types of knitting in different portions of the panty brief. Different types of knitting may be obtained in different portions in the circumferential direction and/or in different regions in the vertical direction.

The machine uses up to six fingers in each system. This makes it possible to obtain threading with different yarns and at the same time it is possible to determine which finger to be used for knitting in the different portions of the panty brief. E.g., it is possible in this manner to knit with cotton plus a wound yarn simultaneously or with two different types of wound yarn. It is possible to combine this knitting in numerous ways by using different types of yarn. While knitting it is possible to form an elastic zone around the leg openings similar to the one used at the waist opening. In practice, however, it is preferred to stitch an elastic waistband along the leg openings simultaneously with the seaming of the crotch area of the panty brief between the two leg openings. There will be no cutting during production of the panty brief and consequently there will only be very little waste of material.

Figure 1:
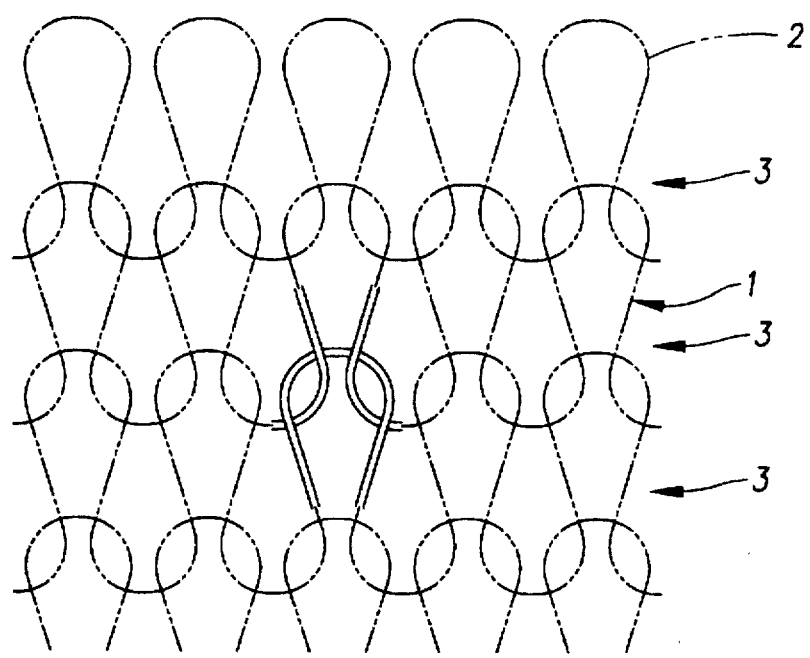
FIG. 1 shows a partial view to illustrate circular knitting such as used for the manufacture of a fixation panty brief according to the invention, FIG. 2 an enlarged fragmentary view of a section of a panty brief according to the invention, FIG. 3 a schematic view to illustrate a first embodiment of a fixation panty brief according to the invention, FIG. 4 a schematic view to illustrate a second embodiment of a fixation panty brief according to the invention, FIG. 5 a schematic view to illustrate a third embodiment of a fixation panty brief according to the invention, and FIG. 6 a schematic view to illustrate a fourth embodiment of a fixation panty brief according to the invention.

FIG. 1 shows a schematic view to illustrate the formation of stitches 1 through the production of loops 2 in circular knitting. Thus, circumferentially extending wales 3 are formed.

Figure 2:
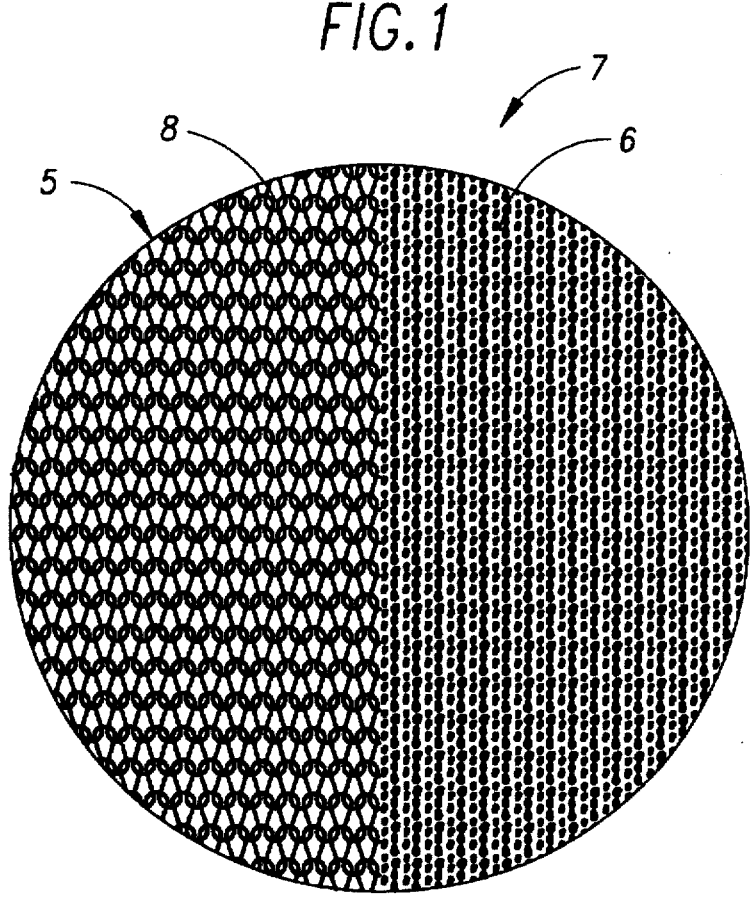
Figure 4:
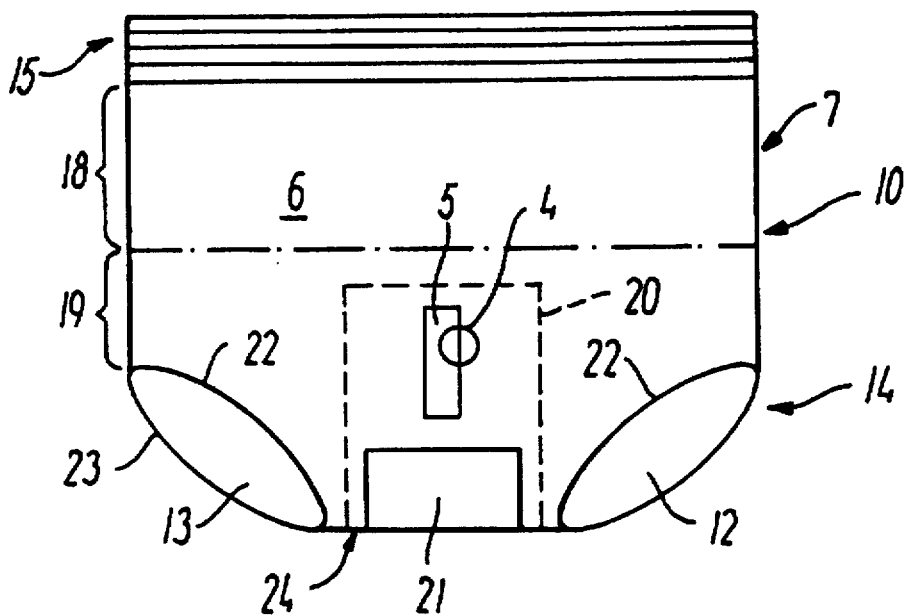

FIG. 2 illustrates an enlarged fragmentary view taken in the region marked at 4 in FIG. 4. FIG. 2 thus illustrates a window area 5. The window area 5 is positioned on a front 6 of a panty brief 7. In the window 5 the stitches 8 have a loose net-like structure so that a transparent area appears, a so-called window. Through this window it is possible to see a moisture indicator placed on a diaper 20 (see FIG. 4), which is intended for fixation during use of the panty brief 7. Thus it is made possible to see from the outside whether it is necessary to change the diaper. The window 5 may, for example, be knitted using every fourth or every second needle so that only needles with thin yarns are used. In this manner the open net-like structure is obtained. It should be noted that a window corresponding to the window 5 on the front 6 of the panty brief may also be knitted into the back of the panty brief for a corresponding visual inspection of a moisture indicator on the back of the diaper.

Figure 3:
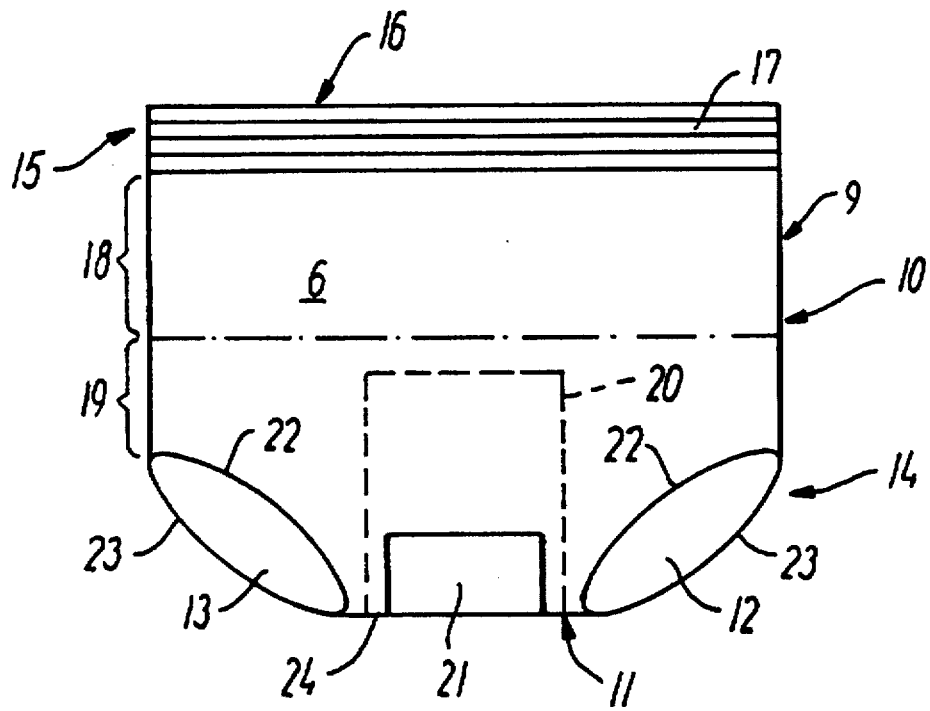

FIG. 3 illustrates a first embodiment of a panty brief 9. This embodiment is produced as a basic model of a lady's panty brief without insertion of an inspection window 5. The panty brief 9 is a diaper fixation panty brief. It comprises a tubular body portion 10 and a crotch portion 11 situated between two leg openings 12,13 at one end 14 of the tubular body portion 10. At the other end 15 of the tubular body portion there is provided a waistband portion 16. The waistband portion 16 is manufactured as a rolling-up free ribbed edge 17 knitted in cotton. Furthermore, the ribbed edge 17 is manufactured using in every second or every fourth system a strong elastic or a wound yarn, e.g. nylon-lycra, in order to obtain the required elasticity in the waistband portion 16. By using yarns of different colours in different systems in the double ribbed edge 17 it is possible to knit in a logo, size indication, washing instructions or other information. Alternatively, it is also possible to knit in a pattern.

The tubular body portion 10 of the panty brief 9 is knitted with a relatively firm and dense knitting in order to provide a tight fit to the user. The body portion 10 is knitted with cotton and nylon and polyester as well as wound yarn, e.g. nylon-lycra, as threads in the different systems. By using different threads it is possible to provide different firmness and elasticity in the knitting. Thus, it is possible to produce the panty brief with increasing elasticity in the upper part 18 of the body portion 10. In the lower part 19 of the body portion 10 a knitting is used which substantially corresponds to the knitting used in the upper part 18. However, in the lower part 19 of the body portion a more elastic wound yarn is used or possibly several systems with elastic wound yarn are used so that the tissue is able to provide better pressure on the diaper 20 the location of which is indicated. In the crotch area 11 between the two leg openings 12 and 13 a looser knitting is used in order to provide a containment and fixation pocket 21 for the central part of the diaper 20.

The containment and fixation pocket 21 is delimited by the remaining knitting in the lower part 19 and in the crotch portion 11. As mention above, in this knitting there is provided an elastic and firm knitting for providing a tight fit to the user's body. In this manner a safe fixation is obtained for a diaper in the pocket 21 situated in the crotch area 11 between the two leg openings 12 and 13.

The illustrated panty brief is assumed to be seen from the front and at the front the leg openings 12,13 are delimited by the line 22 and at the back by the line 23. This illustrates that the panty brief is manufactured with larger width at the back and shorter width at the front in order to provide a better fit to the user.

By using the step motors mounted in the circular knitting machine it is possible to control the stitch length in order to obtain a looser and firmer knitting in various areas of the panty brief. This makes it possible to obtain the tight and snug fit to the user's body in the areas adjacent the pocket 21 at the same time as a loosely knitted pocket 21 is provided which prevents the diaper from being displaced.

FIG. 4 illustrates a second embodiment of a fixation panty brief 7 according to the invention. The panty brief 7 corresponds substantially to the embodiment shown in FIG. 3 and accordingly corresponding and identical parts will not be explained. The panty brief in FIG. 4 differs in that it is provided with a window 5, as explained above with reference to FIG. 2. In FIG. 4 only one window 5 is seen on the front of the panty brief but a similar window may be provided on the back of the panty brief.

The embodiments of the panty brief 7,9 illustrated in FIGS. 3 and 4 are shown with leg openings which are not provided with an actual edge band. Thus these panty briefs are produced in separate units on a circular knitting machine in which the panty brief, after leaving the machine, is stitched along a line 24 and simultaneously provided with a stitched elastic along the leg openings 12,13. In the illustrated embodiments the elastics in the leg openings are left out for simplicity.

Figure 5:
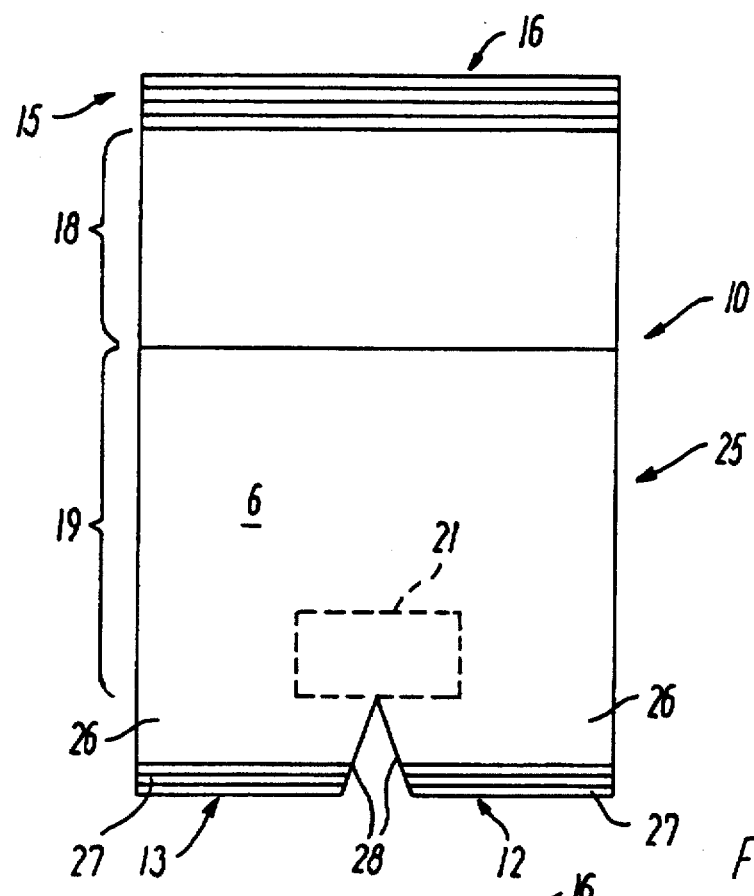

FIG. 5 illustrates a third embodiment of a fixation panty brief 25 according to the invention. The panty brief 25 corresponds substantially to the embodiment illustrated in FIG. 3. The panty brief 25 is produced as a basic model of a gentleman's panty brief with legs 26. However, the panty brief 25 may also be used as a lady's panty brief. Those parts that are identical to the embodiment shown in FIG. 3 are provided with the same reference numerals and will not be explained further. The panty brief 25 is produced with a leg edge band as finish on either leg 26. The leg edge band is knitted as a double ribbed knitting substantially corresponding to the knitting of the ribbed edge 17 explained above. However, the leg edge band 27 must not be knitted too tightly. The panty brief 25 is provided with a containment and fixation pocket 21 with a looser knitting. The pocket 21 may optionally extend along the front and the back for containing an ordinary diaper. Alternatively, in a gentleman's panty brief a fixation pocket 21 may be provided only at the front of the panty brief being intended for containing a diaper used by urinary incontinent male persons. In this situation the pocket will typically have a substantially triangular shape (not shown) adapted to such a diaper.

The panty brief is seamed in the crotch area along the lines 28. This seaming, which is performed simultaneously with a cutting for providing the separation of the legs 26, is the only kind of afterfashioning performed in the shown panty brief. Thus, no cutting out is performed and consequently there will be no material waste. The embodiment shown in FIG. 5 may be modified and manufactured with a window 5 corresponding to the one shown in FIG. 4.

Figure 6:
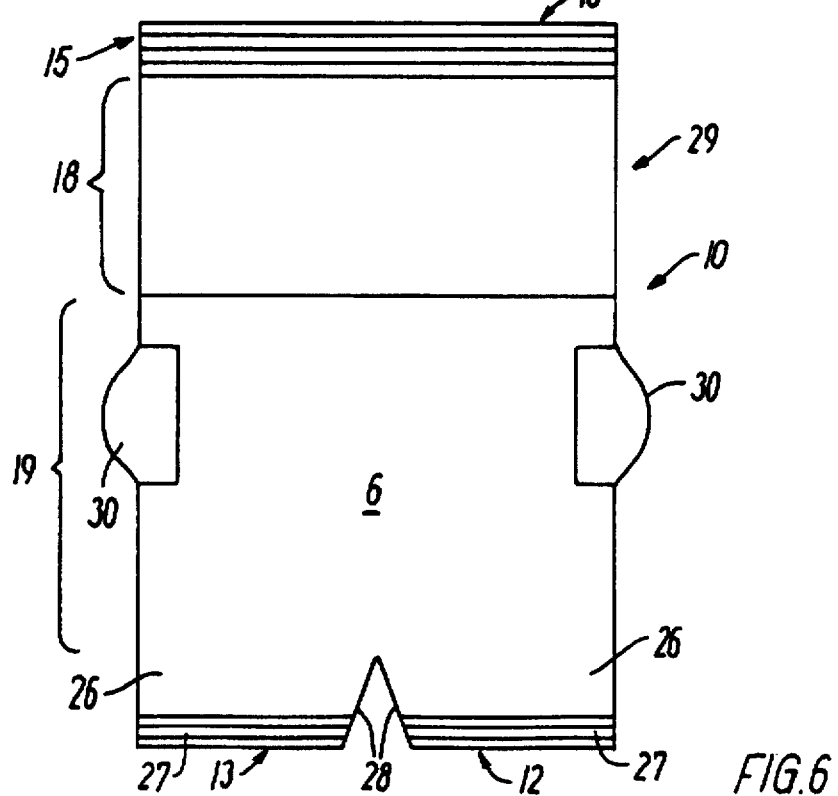

FIG. 6 illustrates a fourth embodiment of a fixation panty brief 29 according to the invention. The panty brief 29 corresponds substantially to the embodiment shown in FIG. 5 but differs in the manner in which the containment and fixation pocket is positioned. In the panty brief 29 two fixation pockets 30 are provided in the area of the panty brief which will be adjacent the hip sockets of the user when in use. Thus, the panty brief 29 is a fixation panty brief for hip protectors primarily used by elderly persons for protection against fractures in the hipbones. The fixation pockets 30 are knitted in as loose areas in the otherwise elastic and firm basic web knitted in the body portion 10.

When knitting the pockets 30, an edge mark may be knitted in to secure that the hip protection bowls are positioned correctly in the pockets before they may be secured in the pocket. Securing such bowls in the pockets may be done e.g. by using velcro band. In this case the inside of the pockets 30 will be manufactured in such a manner that they are particularly suitable for hooking velcro hooks. Alternatively, the hip protection bowls may be seamed inside the pockets 30. It is also possible to use the pockets 30 for containing loose hip protection bowls which are held in place only by the loose knitting of the pockets and secured in the pockets by the elastic and firm knitting of the delimiting edge areas which provide a tight fit to the user's body. In the area between the pockets 30 it is also possible to knit in elastic threads extending circumferentially in order to obtain a higher degree of elasticity and thus an improved fixation of the hip protection bowls.

It is possible to modify the embodiment shown in FIG. 6 for use both for fixation of a diaper and for fixation of hip protection bowls. The panty brief 29 may be further modified by inserting a window corresponding to the window 5 as shown in FIG. 4.

A panty brief according to the invention may advantageously be knitted with a large amount of cotton yarn by using cotton yarns on the various systems. At the same time elasticity may be obtained by using elastic threads or wound yarns in the remaining systems of the circular knitting machine. Thus it is possible to produce a panty brief wherein both the body portion 10 and the crotch portion 11 may contain between 10 and 90% cotton yarns, preferably between 80 and 90% cotton yarns. By knitting the panty brief with legs it is made possible to produce waistband portions 16,27 with a firm knitting in which elastic threads are used so that rolling-up free edge bands or ribs are provided along the leg openings and in the waistband portion 15 of the panty brief for adaptation to the user's body. In this case seaming is only required between the leg openings in order to make the fixation panty brief ready for use.

We claim:

1. A fixation panty brief comprising a tubular body portion having first and second ends, a crotch portion situated between two leg openings at said first end of the tubular body portion and a waistband portion at said second end, the body portion and the crotch portion being one singular circular knitted piece, at least one area of the brief being of a more loose knit, said at least one loose knit area comprising at least one containment and fixation pocket, said at least one pocket having delimiting edge areas of an elastic and firm knit for providing a snug fit about said at least one pocket.

2. A fixation panty brief according to claim 1, wherein the containment and fixation pocket is provided in the crotch portion of the brief between the leg openings for containing a diaper and that the body portion is formed with a close knit containing from about 10% to about 90% cotton yarn.

3. A fixation panty brief according to claim 2, wherein said panty brief has a side which is directed toward the front when in use, the body portion, on said side, having a region with a loose net structure which provides a transparent knitting.

4. A fixation panty brief according to claim 2, wherein said panty brief has both a front and back, elastic threads being interknitted which secure the edge areas of the containment and fixation pocket and which extend upward into the body portion at the front and back of the panty brief.

5. A fixation panty brief according to claim 1, wherein the body portion is formed with a close knit, the body portion having two hip areas and having one of said loose knit areas in each of said hip areas, said loose knit areas comprising containment and fixation pockets for the containment of hip protectors.

6. A fixation panty brief according to claim 5, wherein said fixation panty brief has both a front and back, elastic threads being interknitted which secure the edge areas of the containment and fixation pockets and which extend circumferentially at the front and the back of the panty brief.

7. A fixation panty brief according to claim 1, wherein the body portion contains from about 10% to about 90% cotton yarn.

8. A fixation panty brief according to claim 1, wherein both in the body portion and the crotch portion threads are interknitted which only extend over part of the circumference.

9. A fixation panty brief according to claim 1, wherein the inside of the at least one containment and fixation pocket is of a knit which allows fastening a diaper or a hip protector thereto.

10. A fixation panty brief according to claim 1 including edge bands around the leg openings and in the waistband portion, constituting a firmer knit of elastic threads.

11. A fixation panty brief according to claim 1 wherein the body portion contains from about 80% to about 90% cotton yarn.

* * * * *

UNITED STATES PATENT AND TRADEMARK OFFICE
CERTIFICATE OF CORRECTION

PATENT NO. : 5,671,615
DATED : September 30, 1997
INVENTOR(S) : Finn Kjaergaard
Johannes Nyvang Kristensen It is certified that error appears in the above-indentified patent and that said Letters Patent is hereby corrected as shown below:

Column 6, line 65, (claim 11), "yam." should read --yarn.--

Signed and Sealed this

Sixth Day of January, 1998

Attest:

BRUCE LEHMAN

Attesting Officer

Commissioner of Patents and Trademarks